United States Patent [19]

Brown et al.

[11] Patent Number: 5,373,016
[45] Date of Patent: Dec. 13, 1994

[54] PROTECTION OF ISOTHIAZOLINONE BIOCIDES FROM FREE RADICALS

[75] Inventors: Scott A. Brown, Bear, Del.; Terry Young, Sicklerville, N.J.

[73] Assignee: Zeneca, Inc., Wilmington, Del.

[21] Appl. No.: 68,459

[22] Filed: May 28, 1993

[51] Int. Cl.$^5$ ............................................. A01N 43/80
[52] U.S. Cl. ................................... 514/372; 514/373; 548/209; 548/213
[58] Field of Search ............... 548/209, 213; 514/372, 514/373

[56] References Cited

U.S. PATENT DOCUMENTS

| | | | |
|---|---|---|---|
| 4,906,274 | 3/1990 | Mattox | 514/373 |
| 4,920,137 | 4/1990 | Segall et al. | 514/372 |
| 5,004,749 | 4/1991 | Jerusik et al. | 514/372 |
| 5,108,500 | 4/1992 | Mattox | 514/372 |
| 5,127,934 | 7/1992 | Mattox | 514/372 |
| 5,153,213 | 10/1992 | Schmidt | 514/372 |
| 5,180,514 | 1/1993 | Farr et al. | 252/99 |
| 5,185,356 | 2/1993 | Backhouse et al. | 514/372 |
| 5,246,979 | 9/1993 | Lutz et al. | 522/42 |

FOREIGN PATENT DOCUMENTS 861379 2/1961 United Kingdom.
2176187 12/1986 United Kingdom.

*Primary Examiner*—Joseph Paul Brust
*Assistant Examiner*—MarySusan H. Gabilan
*Attorney, Agent, or Firm*—Panitch Schwarze Jacobs & Nadel

[57] ABSTRACT

Biocidal isothiazolinone or isothiazolothione compounds are stabilized with an effective amount of a free-radical scavenger compound. Exemplary of the biocidal isothiazolones are 1,2-benzisothiazolin-3-one, 2-methyl-4-5-trimethylene-4-isothiazolin-3-one, 5-chloro-2-methyl-4-isothiazolin-3-one and 2-methyl-4-isothiazolin-3-one. Effective free-radical scavengers include 3,3-thiodipropionic acid.

11 Claims, 4 Drawing Sheets

PROTECTION OF ISOTHIAZOLINONE BIOCIDES FROM FREE RADICALS

FIELD OF THE INVENTION

The present invention relates to an isothiazolinone or isothiazolothione biocide composition stabilized against attack by free radicals and a method for stabilizing the biocides.

BACKGROUND OF THE INVENTION

Biocides are substances that kill or inhibit the growth of microorganisms such as bacteria, fungi and algae. Biocidal chemicals include chlorinated hydrocarbons, organometallics, halogen-releasing compounds, metallic salts, quaternary ammonium compounds, phenolics and organic sulfur compounds.

Exemplary of organic sulfur compounds are compounds based on an isothiazolinone or isothiazolothione structure. The biocidal activity of these compounds is effected by inactivation of essential enzymes of microbial metabolism which require sulfhydryl groups for activity. These enzymes include phosphoenolpyruvate transphosphorase and a number of dehydrogenases. The thio moiety of the isothiazolinone or isothiazolothione compounds reacts with the free sulfhydryl groups of an enzyme to form a disulfide bond between the enzyme molecule and the isothiazolinone or isothiazolothione molecule rendering the sulfhydryl unavailable for interaction with substrate or effector molecules.

Isothiazolinone and isothiazolothione biocides have found widespread use as latex preservatives. Most latex emulsions are water based and are prone to microbial attack. Biocides are typically added to the finished latex after all processing is completed to protect the latex from microbial attack.

Manufacture of latex by emulsion polymerization requires certain free-radical generating chemicals to initiate polymerization. At elevated temperatures, these radical-generating compounds undergo homolytic decomposition to form active free radicals which participate in the propagation reaction which makes polymerization possible. Several different types of thermal initiators are currently in use; exemplary are azo compounds and peroxy compounds such as 2,2'-azobisisobutyronitrile, peroxydisulfate ion, benzoyl peroxide and t-butyl hydroperoxide. Alternatively, polymerization can be initiated with a redox initiator system containing an oxidizing and a reducing agent. The redox systems also generate free radicals; exemplary are ferrous ion with hydrogen peroxide, sodium formaldehyde sulfoxylate, sodium thiosulfate and sodium metabisulfite.

During the manufacture of latex, the polymerization process is rarely allowed to proceed to 100% monomer to polymer conversion due to the negative effect of excessive chain branching and molecular weight distribution on polymer structure when conversions approach 100%. Post-polymerization latex therefore contains a substantial amount of monomer.

Recently, latex manufacturers have increased their efforts to reduce the monomer content of finished latex to increase latex emulsion stability. Redox systems, such as those described above or t-butyl hydroperoxide and a bisulfite salt or thermal initiators as described above are often added to latex after polymerization to reduce the monomer content. The systems act to generate free radicals and activate residual monomers which are then bonded by an addition reaction to the polymer bringing the free monomer concentration to around 0.1% or less. The redox system components or other radical-generating chemicals which are added to the latex, either to initiate polymerization or to reduce post-polymerization monomer content are largely consumed by these reactions. However, finished latex still contains some residual amount of these radical-generating chemicals. It has been found that the residual radical-generating chemicals react with the active ingredients of biocide formulations and destroy their biocidal activity.

Biocides which are widely used as latex preservatives include PROXEL® GXL, having an active ingredient of 1,2-benzisothiazolin-3-one (BIT), PROMEXAL® W50, having an active ingredient of 2-methyl-4,5-trimethylene-4-isothiazolin-3-one, both available from Zeneca Inc., and KATHON® LX, a blend of 5-chloro-2-methyl-4-isothiazolin-3-one and 2-methyl-4-isothiazolin-3-one active ingredients, available from Rohm and Haas Company. Decrease in biocidal activity results in a latex that is not sufficiently protected from microbial attack and in reduced cost efficacy of the biocide. Thus, it is desirable to stabilize the biocides used in products and processes where free radicals are generated by stabilizing the biocides against free-radical degradation.

While organic stabilizers for isothiazolinones such as orthoesters and epoxy compounds have been disclosed in U.S. Pat. Nos. 4,906,274 and 5,127,934, respectively, these patents are directed specifically to protection of isothiazolinones from molecules containing nucleophilic groups. Nucleophiles are ions or molecules which can donate a pair or electrons to form a covalent bond with another atom. A molecule containing a nucleophilic group is electron-rich and makes that molecule more likely to donate a pair of electrons for bond formation. In contrast, free radicals are molecular fragments which have one or more unpaired electrons and in a reaction, seek to acquire a single additional electron. Thus, free radicals are not considered to be nucleophiles and the isothiazolinone stabilizers of the prior art would not protect the compounds from attack and degradation by free radicals.

Copper salt stabilizers of oil soluble, water insoluble isothiazolinones have been disclosed in U.S. Pat. No. 5,108,500. However, the salts disclosed are not free-radical scavengers.

Clearly, a need exists for compounds which can stabilize isothiazolinone or isothiazolothione biocides, i.e., protect them from free-radical attack and degradation. Such stabilizing compounds would enable the use of decreased amounts of isothiazolinone or isothiazolothione biocides while maintaining biocidal efficacy and improve the cost-effectiveness of the biocidal compounds as preservatives.

SUMMARY OF THE INVENTION

Accordingly, one aspect of the present invention is a stabilized composition comprising a biocidal isothiazolinone or isothiazolothione compound or a salt or complex thereof and a free-radical scavenger in an amount effective to protect the biocidal compound from degradation by free radicals.

Another aspect of the invention is a method for stabilizing a biocidal isothiazolinone or isothiazolothione compound or salt or complex thereof comprising mixing with the biocidal compound a free-radical scavenger in an amount effective to protect the biocidal compound from degradation by free radicals.

BRIEF DESCRIPTION OF THE DRAWINGS

The foregoing Summary, as well as the Detailed Description of the Preferred Embodiments will be better understood when read in conjunction with the appended drawings.

DETAILED DESCRIPTION OF THE PREFERRED EMBODIMENTS

Figure 1:
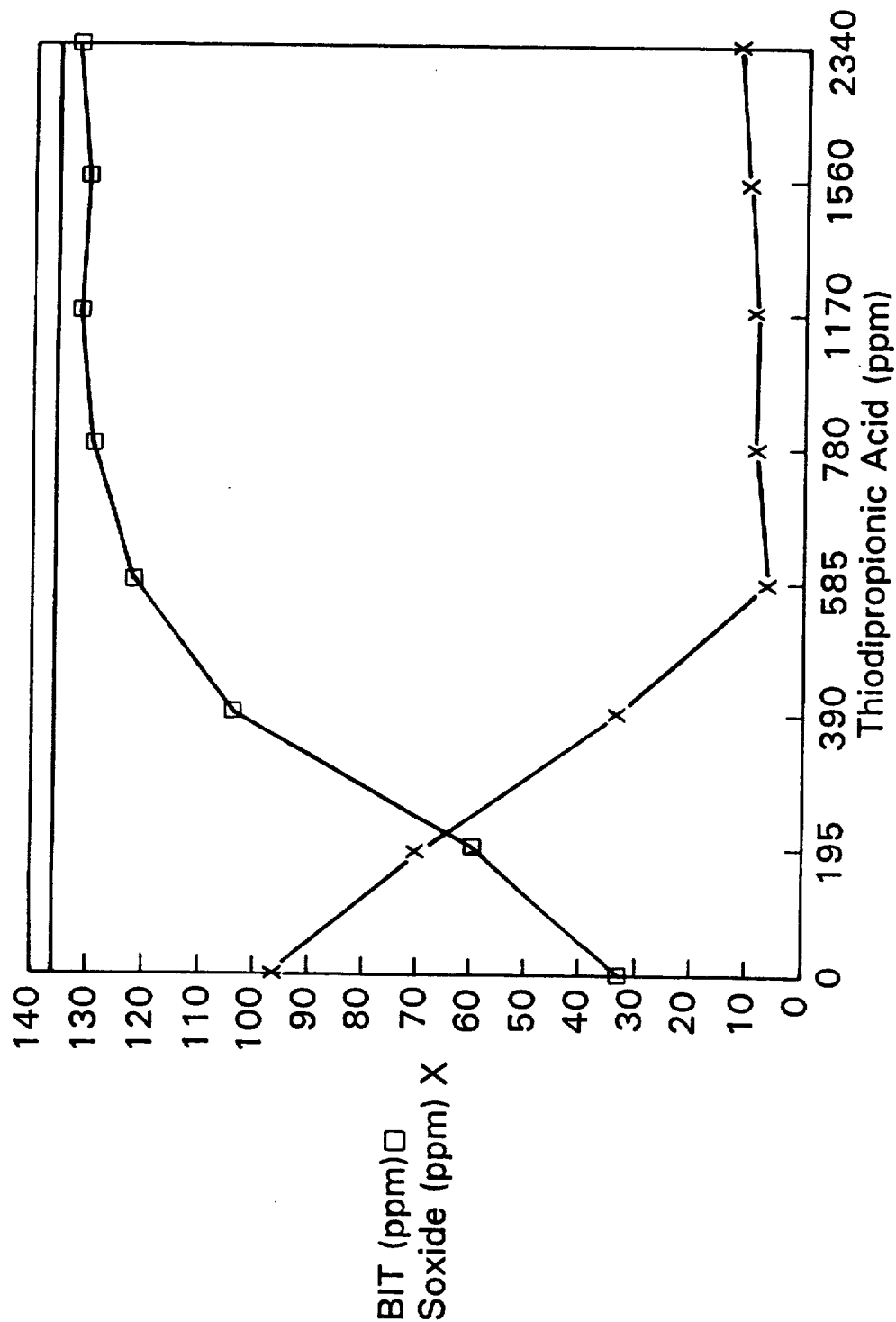
FIG. 1 is a graph demonstrating BIT and its oxidation product (Soxide) concentrations as a function of 3,3-thiodipropionic acid concentration in the presence of a fixed concentration of ammonium persulfate.

The composition and method of the present invention are useful for the protection of biocidal isothiazolinones or isothiazolothiones against degradation by free radicals. The invention provides for stabilized compositions containing a biocidal isothiazolinone or isothiazolothione and a free-radical scavenging compound, where the free-radical scavenger is present in an amount effective to protect the biocidal compound from degradation by free radicals. The biocidal compounds protected include isothiazolinones or isothiazolothiones or a salt or complex thereof.

The isothiazolinones or isothiazolothiones of the present invention are represented by the general formula (I):

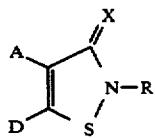

(I)

or a salt or a complex thereof; wherein
X is oxygen or sulfur;
R is hydrogen, a substituted or unsubstituted hydrocarbyl group, a substituted or unsubstituted hydrocarbylthio group, a substituted or unsubstituted hydrocarbyloxy group or a carbamoyl group; and
each of A and D is independently hydrogen, a halogen atom, a cyano group, a substituted or unsubstituted hydrocarbyl group or a direct bond to the other of A or D.

When R, A and D are, or contain, substituted hydrocarbyl groups, the substituents are preferably independently halogen, alkoxy or alkylthio where the alkyl groups contain 1 to 4 carbon atoms. If R is a carbamoyl group, preferably it is of the general type —CON(H)(R$^1$) where R$^1$ is a hydrogen atom or a hydrocarbyl group, which may be substituted with halogen, alkoxy or alkylthio substituents. It is generally preferred that R is a hydrogen atom or a lower alkyl group of 1 to 4 carbon atoms. Most preferably, R is hydrogen or a methyl group.

Preferably, A and D, together with the carbon atoms to which they are attached, form a five- or six-membered substituted or unsubstituted ring. The ring substituents are preferably halogen, alkyl of 1 to 4 carbon atoms, alkoxy of 1 to 4 carbon atoms or alkylthio of 1 to 4 carbon atoms. The ring may contain a heteroatom such as a nitrogen atom replacing a carbon atom. Most preferably, A and D form a hydrocarbon ring such as benzene, cyclopentene or cyclohexene.

Alternatively, A and D are separate groups. Preferably, at least one of A and D is not a hydrogen atom and most preferably, at least one of A and D is a halogen atom or an alkyl group of 1 to 4 carbon atoms.

The biocidal isothiazolinone compounds include 5-chloro-2-methyl-4-isothiazolin-3-one (where R is methyl, A is hydrogen and D is chlorine); 2-methyl-4-isothiazolin-3-one (where R is methyl and A and D are both hydrogen); 4,5-dichloro-2-methylisothiazolin-3-one (where R is methyl and A and D are both chlorine); 2-n-octylisothiazolin-3-one (where R is n-octyl and A and D are both hydrogen; 1,2-benzisothiazolin-3-one (where R is hydrogen and A and D, together with the carbon atoms to which they are attached, form a benzene ring); 4,5-trimethylene-4-isothiazolin-3-one (where R is hydrogen and A and D, together with the carbon atoms to which they are attached, form a cyclopentene ring) and 2-methyl-4,5-trimethylene-4-isothiazolin-3-one (where R is methyl and A and D, together with the carbon atoms to which they are attached, form a cyclopentene ring).

Most preferably, the biocidal compound is one where R is hydrogen and A and D together form an unsubstituted 5- or 6-membered hydrocarbon ring as in the compounds 1,2-benzisothiazolin-3-one and 4,5-trimethylene-4-isothiazolin-3-one.

Certain of the isothiazolinone or isothiazolothione compounds which may be used as the biocidal compound can have improved solubility in water when in the form of a salt or complex. The salt or complex may be with any suitable cation such as an amine (including an alkanolamine) or a metal. Preferably, any metal salt or complex contains a monovalent metal such as an alkali metal. The alkali metal may be lithium, sodium or potassium. Most preferably, the alkali metal salt is a sodium salt in view of the ready availability of suitable sodium compounds from which to prepare the salt.

Certain isothiazolinone or isothiazolothione compounds useful as the biocidal compounds decompose in the presence of alkali. Exemplary of alkali-sensitive compounds are 5-chloro-2-methyl-4-isothiazolin-3-one and 2-methyl-4-isothiazolin-3-one. Accordingly, the pH of the compositions of the present invention which are alkali sensitive should be maintained at a value no greater than about 8. The pH may be controlled by addition of inorganic compounds such as ammonia, sodium hydroxide, potassium hydroxide, sodium carbonate and potassium carbonate.

The free-radical scavenger compounds used in the invention include compounds which protect isothiazolinones from attack and degradation by free radicals generated by compounds which undergo homolytic decomposition to form active free radicals and redox initiator systems having an oxidizing and a reducing agent. Exemplary of the free-radical scavengers are antioxidant compounds. Preferably, the free-radical scavenger compounds include 3,3-thiodipropionic acid, L-ascorbic acid, D-ascorbic acid, fumaric acid, diethylhydroxylamine, glutaraldehyde, butyraldehyde, L-tartaric acid, 4-methoxyphenol and propyl gallate. Most preferably, the free-radical scavenger is 3,3-thiodipropionic acid.

The stabilized compositions of the invention contain at least one biocidally active isothiazolinone or isothiazolothione as described above and at least one free-radical scavenger. Typical formulation ranges are illustrated in Table 1 for both concentrated and dilute solutions of the stabilized isothiazolone or isothiazolothione. All percentages in Table 1 are approximate percentage by weight. Formulation range 2 represents a preferred embodiment; formulation range 3 represents a more preferred embodiment.

TABLE 1

| Formulation Range | Formulation Ranges | | |
|---|---|---|---|
| | Biocide Active Agent | Radical Scavenger | Solvent |
| 1 | 0.1–99.9% | 0.1–99.9% | 0–99.8% |
| 2 | 1–50% | 1–25% | 25–98% |
| 3 | 1–25% | 1–10% | 65–98% |

The stabilized compositions of the invention are typically used at any locus subject to contamination by bacteria, fungi or algae where free-radicals are likely to be present. While the principal application of the stabilized compositions may be in production of latices such as acrylic, vinyl acetate acrylic, polyvinyl acetate, styrene butadiene and silicone, applications are also possible in paints, leather- and wood-treatment fluids, metalworking fluids, cooling water and plastics materials and many other applications where water and organic materials are present under conditions which allow the growth of undesired microorganisms.

The present invention will now be illustrated in more detail by reference to the following, specific, non-limiting examples.

EXAMPLES

The protection of biocide active 1,2-benzisothiazolin-3-one (BIT) by free-radical scavenging compounds against free-radical-induced degradation was evaluated in Examples 1–5. Known amounts of radical generator, radical scavenger and biocide were prepared and biocide-active compound remaining after an incubation period determined. The radical generators and radical scavengers are identified in each experiment. The biocide formulation was PROXEL® GXL which is an aqueous dispersion of approximately 19% BIT in dipropylene glycol and water. The BIT content of the samples was measured by high pressure liquid chromatography (HPLC) on a HYPERSIL® ODS column (4.6 mm×25 cm) eluted isocratically at flow rate of 1.5 ml/min with 77% water, 11% acetonitrile, 9% methanol and 3% glacial acetic acid. Retention time for BIT is approximately 7.5 minutes. The content of 1,2-benzisothiazolin-3-one sulfoxide, hereinafter "Soxide," a compound produced by the oxidation of BIT, was also measured by HPLC under the same conditions. Retention time for Soxide is approximately 3 minutes. Soxide is the principal compound formed from free-radical attack on BIT.

Example 1

Scavenger Screening in Water

Radical scavengers were screened for their BIT protective activity in water. Aqueous solutions of a radical-generating compound, a radical-scavenger compound and dilutions of BIT (PROXEL® GXL) in water were prepared. The stock solutions were mixed so that the radical-generating compound ("Radical" in Table 2), the radical scavenger compound ("Scavenger" in Table 2) and the BIT were present in approximately equal amounts by molar ratio.

The three separate stock solutions were heated to 60° C. in a water bath and equal volumes of the radical-generator solution and the radical-scavenger solution were mixed together and reacted for 1 hour at 60° C. The heated, mixed solution was then mixed with an equal volume of dilute PROXEL® GXL solution. This mixture was reacted for 1 hour at 60° C. At the end of the reaction time, the solution was further diluted and analyzed for BIT and Soxide by HPLC.

Three controls were run for each experimental run. All of the components were contained in each experimental run. The radical control contained only the radical generator and BIT; the scavenger control contained only the radical scavenger and BIT; the BIT control contained only BIT. The radical generators used were either t-butyl hydrogen peroxide (TBHP) or ammonium persulfate (APS). In one experimental run, the scavenger compound 3,3-thiodipropionic acid was buffered with phosphate to a pH of approximately 8.

TABLE 2

| | BIT Protection in Water | | | | | | |
|---|---|---|---|---|---|---|---|
| Scavenger | Radical | % A[(1)] | Exptl. Run | Radical Control | % D[(2)] | Scavenger Control | BIT Control |
| L-Ascorbic | TBHP | 98% | 962 | 268 | 72.5% | 959 | 974 |
| Glutaraldehyde | APS | 28% | 371 | 146 | 84.7% | 985 | 952 |
| L-Ascorbic acid | APS | 28% | 362 | 130 | 86.3% | 961 | 950 |
| D-Ascorbic acid | APS | 87% | 923 | 193 | 81.4% | 1026 | 1034 |
| 3,3 Thiodipropionic acid* | TBHP | 102% | 969 | 282 | 70.4% | 971 | 954 |
| 3,3 Thiodipropionic acid* | APS | 98% | 950 | 154 | 84.0% | 747 | 964 |
| Butyraldehyde | TBHP | 14% | 420 | 321 | 69.2% | 1051 | 1042 |
| Butyraldehyde | APS | 31% | 447 | 189 | 81.4% | 1003 | 1017 |
| 3,3 Thiodipropionic acid + | APS | 92% | 968 | 151 | 85.4% | 1014 | 1037 |
| L-Tartaric acid | APS | 33% | 507 | 223 | 79.3% | 1067 | 1076 |
| 4-Methoxyphenol | APS | 57% | 692 | 206 | 80.4% | 1134 | 1052 |

TABLE 2-continued

| | | BIT Protection in Water | | | | | |
|---|---|---|---|---|---|---|---|
| Scavenger | Radical | % A[1] | Exptl. Run | Radical Control | % D[2] | Scavenger Control | BIT Control |
| Propyl Gallate | APS | 57% | 659 | 204 | 79.7% | 1007 | 1005 |

[1]The % A column reflects the activity of the scavenger. The formula for calculating % A is (Experimental Run - Radical Control)/(BIT Control - Radical Control) × 100.
[2]The % D column reflects the amount of initial BIT degraded by the radical in the absence of scavenger, i.e., 1 - (Radical Control/BIT Control) × 100. All other values are ppm BIT.
*Unbuffered
+ Buffered The experimental results presented in Table 2 indicate that the listed free-radical scavenger compounds are active as BIT protectants in water. The activity of the listed scavenger compounds ranged from 14% to 102%±the experimental error of the protocol. The scavenger control results also indicate that none of the listed scavenger compounds resulted in any significant degradation of BIT with the exception of unbuffered 3,3-thiodipropionic acid. Unbuffered 3,3-thiodipropionic acid resulted in an approximately 23% decrease in the measured BIT concentration where APS was the radical generator. This result is believed to be due to decreased solubility of BIT at low pH. Comparison of the radical control results to the BIT control results in all of the experiments indicates that ammonium persulfate and t-butyl hydroperoxide result in an approximately 70 to 86% degradation of initial BIT.

Examples 2–5

BIT Protection in Latex Emulsion A common experimental design was used for testing the scavengers 3,3-thiodipropionic acid, diethylhydroxylamine, L-ascorbic acid and glutaraldehyde as BIT protectants in the presence of a latex emulsion. All samples and controls were prepared and analyzed by HPLC in duplicate. The experimental conditions, for Example Nos. 2–5, are given in Table 3.

TABLE 3

| Example No. | Scavenger | Scavenger, ppm | Radical | Radical, ppm | BIT, ppm |
|---|---|---|---|---|---|
| 2 | 3,3-thiodipropionic acid | 195 | Ammonium persulfate | 1000 | 132 |
| | | 390 | | | |
| | | 585 | | | |
| | | 780 | | | |
| | | 1170 | | | |
| | | 1560 | | | |
| | | 2340 | | | |
| 3 | diethylhydroxyamine (DEHA) | 500 | t-butyl hydrogen peroxide | 2000 | 304 |
| | | 1000 | | | |
| | | 1500 | | | |
| | | 2000 | | | |
| | | 2500 | | | |
| 4 | L-ascorbic acid | 500 | t-butyl hydrogen peroxide | 2000 | 304 |
| | | 1000 | | | |
| | | 1500 | | | |
| | | 2000 | | | |
| 5 | glutaraldehyde | 250 | ammonium persulfate | 1000 | 285 |
| | | 500 | | | |
| | | 750 | | | |
| | | 1000 | | | |
| | | 1250 | | | |
| | | 1500 | | | |

Latex aliquots from Reichhold Chemicals, Inc. (Example 2) or Dow Chemical Company (Examples 3–5) were placed into sample bottles and shaken with heating to 60° C. A known amount of a radical-generating compound was added. Sample solutions were allowed to return to 60° C. and varying amounts of a radical-scavenger compound were also added to the samples. The samples were allowed to return to 60° C. and then reacted for 1 hour after reaching 60° C. At the end of the one-hour time period, the samples were removed from the heat and allowed to cool to room temperature. After cooling, PROXEL® GXL was added to the samples to provide a known BIT concentration. The samples were shaken overnight and aliquots analyzed by HPLC for BIT and Soxide the following day.

Three types of controls were prepared in a similar manner. A latex control was prepared by omitting the scavenger and radical-generating compounds. A water control was prepared by replacing the latex emulsion with water and omitting the scavenger and radical-generating compounds. A radical control was prepared by omitting the scavenger compound.

Comparison of the latex control to the water control in each of Example Nos. 2–5 indicated that no significant degradation of BIT was occurring as a result of the latex emulsion. The latex controls represent the BIT concentration present initially in each of the experimental samples. The radical controls represent the amount of BIT degraded by the chosen free-radical generator.

Figure 2:
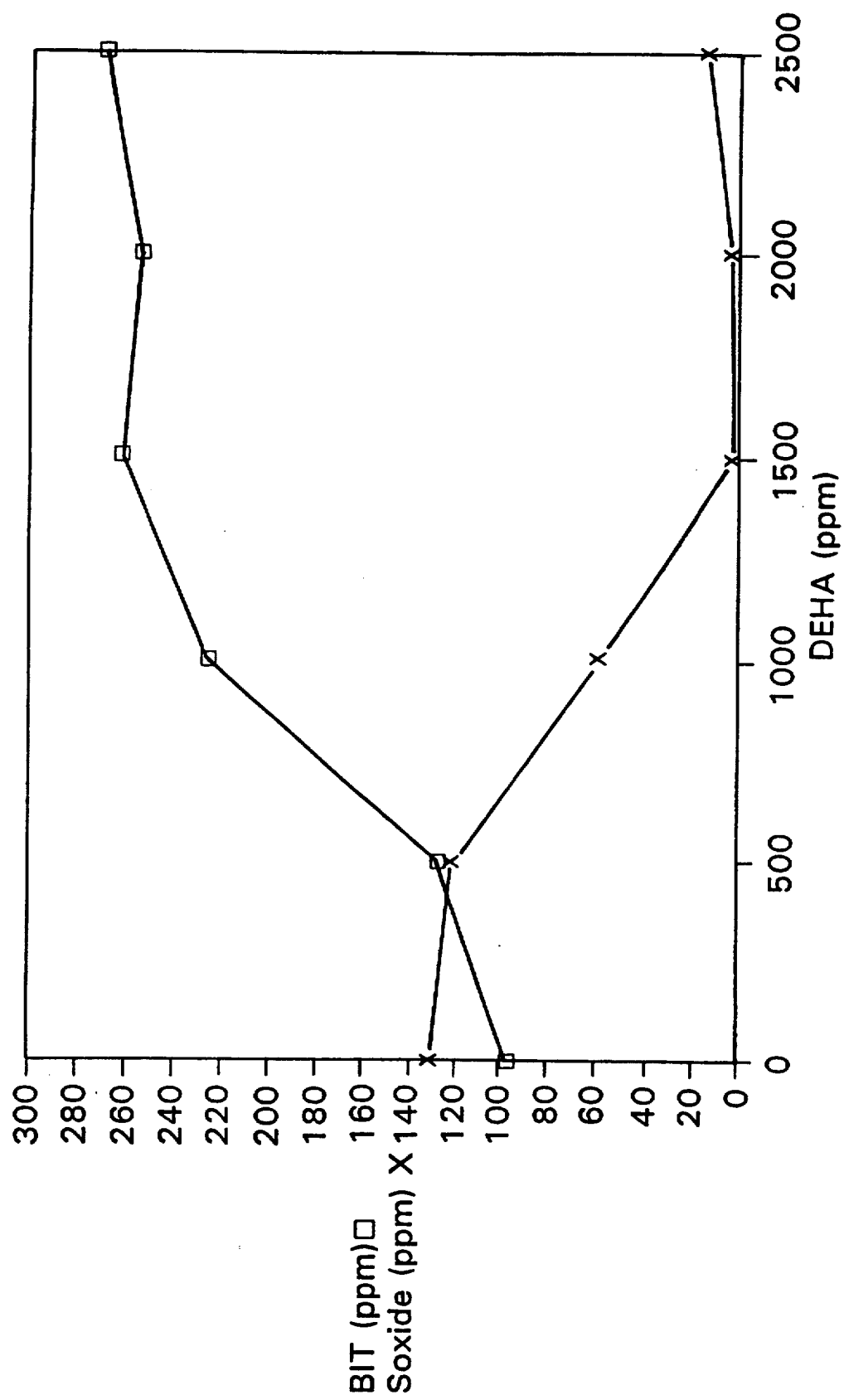
FIG. 2 is a graph demonstrating BIT and Soxide concentrations as a function of diethylhydroxy amine in the presence of a fixed concentration of t-butyl hydrogen peroxide.
Figure 3:
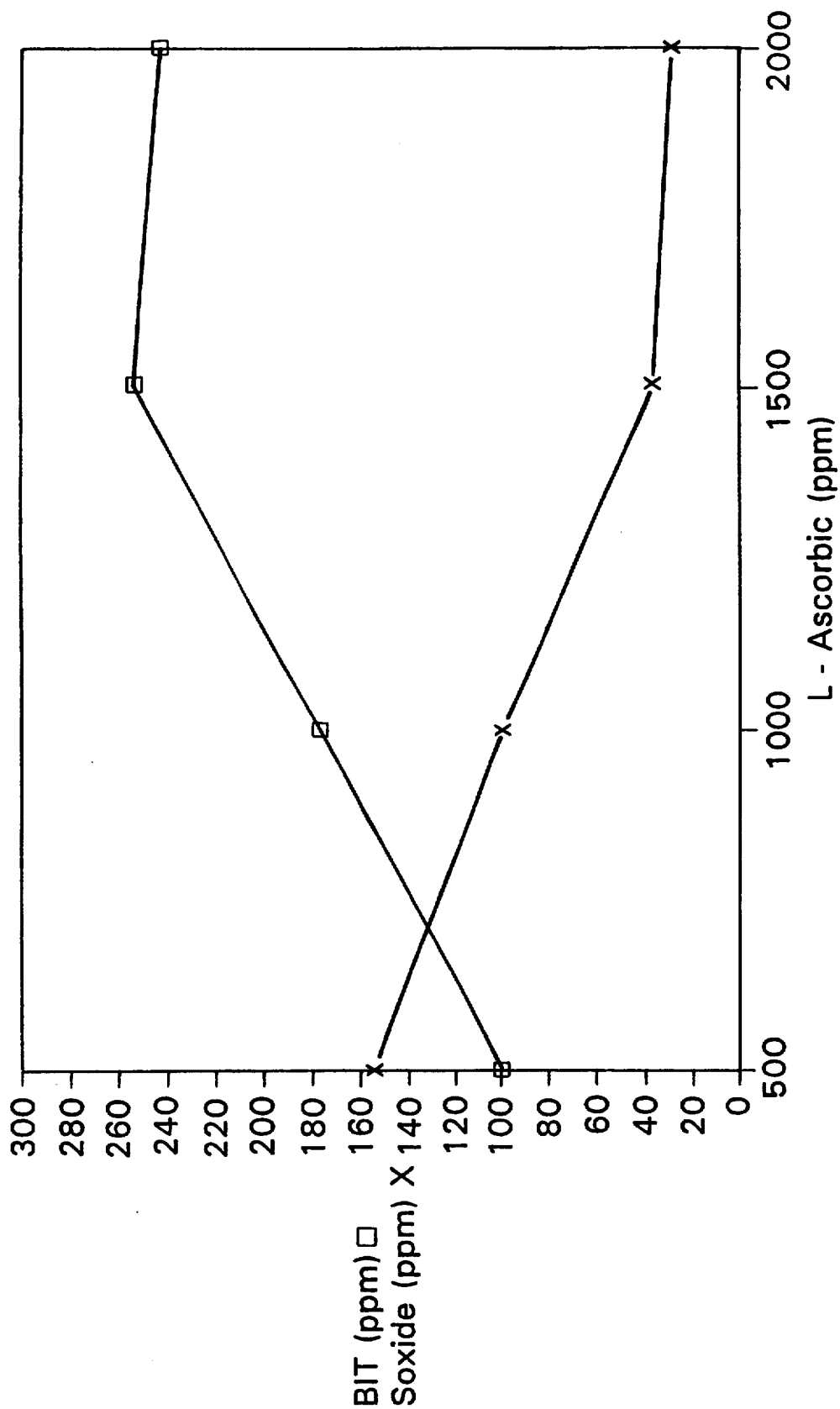
FIG. 3 is a graph demonstrating BIT and Soxide concentrations as a function of L-ascorbic acid concentration in the presence of a fixed concentration of t-butyl hydrogen peroxide.
Figure 4:
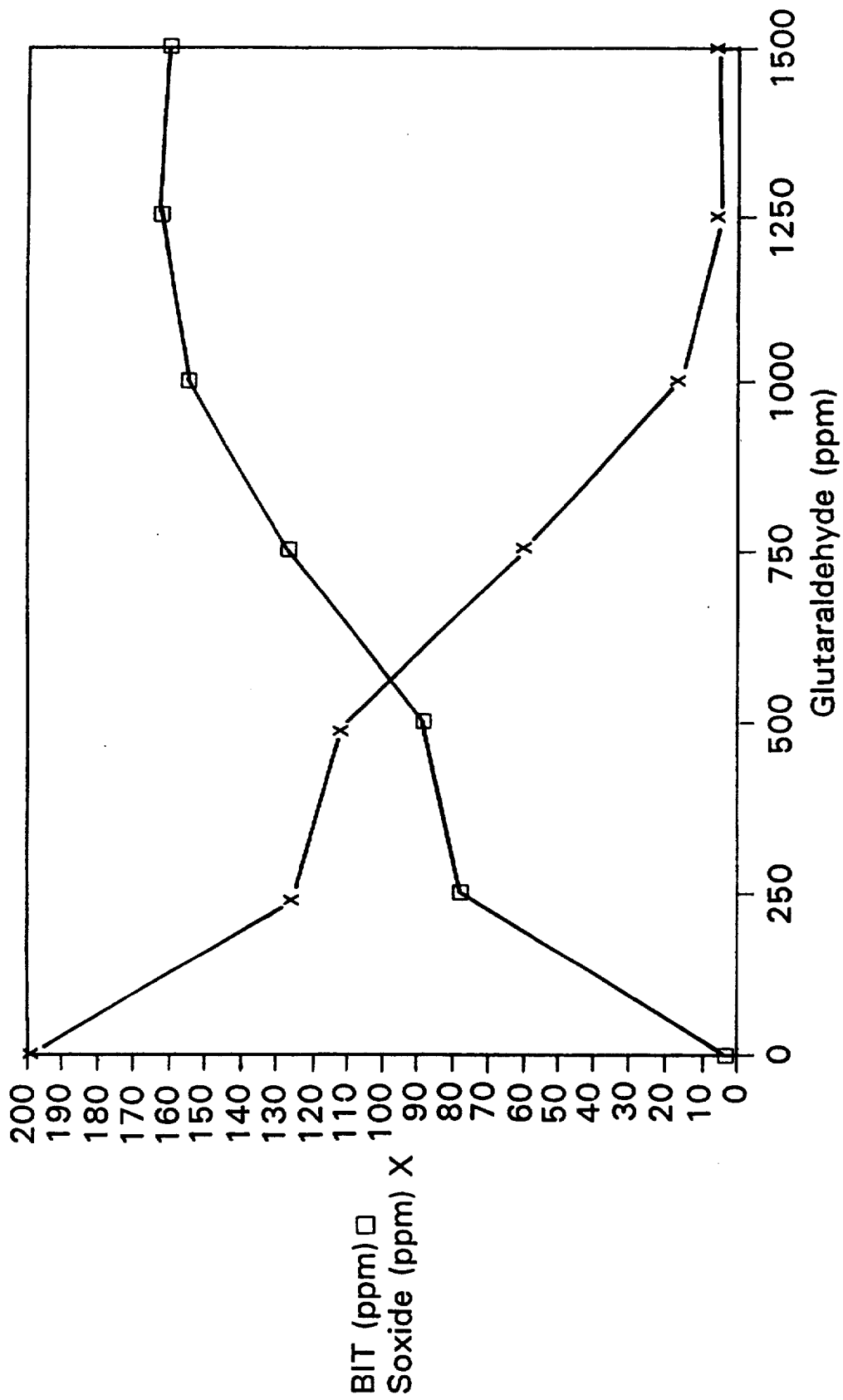
FIG. 4 is a graph demonstrating BIT and Soxide concentrations as a function of glutaraldehyde concentration in the presence of a fixed concentration of ammonium persulfate.

FIGS. 1–4 graphically demonstrate the experimental results of Example Nos. 2–5, respectively. The results demonstrate the effectiveness of the scavenger compounds tested as protective agents for BIT in latex emulsions. The straight line at the top of each Figure represents the latex control value in ppm BIT, except in FIG. 3 where the value (off the graph) was 345 ppm BIT. Increasing the scavenger compound concentration results in an increase of the amount of BIT present. Conversely, in all of the experiments, Soxide concentration decreases as a function of increasing the scavenger compound concentration. Percent oxidation of BIT can be calculated by dividing the radical control BIT value (plotted as 0 ppm scavenger) by the latex control BIT value and subtracting the resultant value from 1. The oxidation of BIT was approximately 76% in Example 2 (FIG. 1), approximately 64% in Example 3 (FIG. 2) and approximately 98% in Example 5 (FIG. 4) in the absence of scavenger. In Example 4 (FIG. 3), the radical control value was anomalous and was not plotted. However, the results plotted in FIG. 3 indicate BIT protection as a function of increasing scavenger concentration. Thus, the results of Example Nos. 2–5 demonstrate that the scavenger compounds function to protect BIT from oxidation and subsequent inactivation.

An additional free-radical scavenger compound expected to be active as an isothiazolinone or isothiazolothione protectant is fumaric acid, a known antioxidant. Preliminary data in experiments using a redox system containing sodium metabisulfite showed BIT protection as a result of increasing fumaric acid concentration.

The present invention may be embodied in other specific forms without departing from the spirit or essential attributes thereof and, accordingly, reference should be made to the appended claims, rather than to the foregoing specification as indicating the scope of the invention.

We claim:

1. A stabilized composition comprising:
   (a) a biocidal compound selected from the group consisting of 1,2-benzisothiazolin-3-one, 2-methyl-4,5-trimethylene-4-isothiazolin-3-one, 5-chloro-2-methyl-4-isothiazolin-3-one, 2-methyl-4-isothiazolin-3-one, salts thereof and complexes thereof; and
   (b) 3,3-thiodipropionic acid in an amount effective to protect the biocidal compound from degradation by free radicals.

2. The stabilized composition according to claim 1 wherein the biocidal compound (a) is selected from the group consisting of 1,2-benzisothiazolin-3-one, salts thereof and complexes thereof.

3. The stabilized composition according to claim 1 wherein the biocidal compound (a) is selected from the group consisting of 2-methyl-4,5-trimethylene-4-isothiazolin-3-one, salts thereof and complexes thereof.

4. The stabilized composition according to claim 1 wherein the biocidal compound (a) is selected from the group consisting of a blend of 5-chloro-2-methyl-4-isothiazolin-3-one and 2-methyl-4-isothiazolin-3-one, salts thereof and complexes thereof.

5. The stabilized composition according to claim 1 comprising from about 0.1 to 99.9 parts of at least one of said biocidal compounds, from about 0.1 to 99.9 parts of 3,3-thiodipropionic acid and from about 0 to 99.8 parts of a solvent.

6. The stabilized composition according to claim 5 comprising from about 1 to 50 parts of at least one of said biocidal compounds, from about 1 to 25 parts of 3,3-thiodipropionic acid and from about 25 to 98 parts of the solvent.

7. The stabilized composition according to claim 6 comprising from about 1 to 25 parts of at least one of said biocidal compounds, from about 1 to 10 parts of 3,3-thiodipropionic acid and from about 65 to 98 parts of the solvent.

8. A method for stabilizing a biocidal isothiazolinone compound or a salt or complex thereof comprising mixing (a) a biocidal compound selected from the group consisting of 1,2-benzisothiazolin-3-one, 2-methyl-4,5-trimethylene-4-isothiazolin-3-one, 5-chloro-2-methyl-4-isothiazolin-3-one, 2-methyl-4-isothiazolin-3-one, salts thereof and complexes thereof with (b) 3,3-thiodipropionic acid in an amount effective to protect the biocidal compound from degradation by free radicals.

9. The method according to claim 8 wherein the biocidal compound (a) is selected from the group consisting of 1,2-benzisothiazolin-3-one, salts thereof and complexes thereof.

10. The method according to claim 8 wherein the biocidal compound (a) is selected from the group consisting of 2-methyl-4,5-trimethylene-4-isothiazolin-3-one, salts thereof and complexes thereof.

11. The method according to claim 8 wherein the biocidal compound (a) is selected from the group consisting of a blend of 5-chloro-2-methyl-4-isothiazolin-3-one and 2-methyl-4-isothiazolin-3-one, salts thereof and complexes thereof.

* * * * *